United States Patent [19]

Radunz et al.

[11] 4,125,622
[45] Nov. 14, 1978

[54] 1,4-OXATHIANES

[75] Inventors: Hans-Eckart Radunz; Dieter Orth; Manfred Baumgarth; Reinhard Lissner; Jürgen Maisenbacher, all of Darmstadt, Fed. Rep. of Germany

[73] Assignee: Merck Patent Gesellschaft mit beschrankter Haftung, Fed. Rep. of Germany

[21] Appl. No.: 860,355

[22] Filed: Dec. 14, 1977

[30] Foreign Application Priority Data

Dec. 24, 1976 [DE] Fed. Rep. of Germany ....... 2658850

[51] Int. Cl.$^2$ ........................................... C07D 327/06
[52] U.S. Cl. .............................. 424/276; 260/327 P; 560/154
[58] Field of Search ..................... 260/327 P; 424/276

Primary Examiner—Norma S. Milestone
Attorney, Agent, or Firm—Millen & White

[57] ABSTRACT 1,4-Oxathianes of the formula

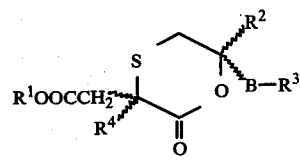

and the physiologically-acceptable salts thereof wherein $R^1$ is H or alkyl with 1–4 C-atoms; $R^2$ is H or alkyl with 1–4 C-atoms; $R^3$ is H, alkyl with 1–8 C-atoms, phenyl or phenyl substituted by F, Cl, Br, OH, OCH$_3$, CF$_3$ or NO$_2$; $R^4$ is H or CH$_3$; B is a single bond, —CH$_2$—, —CH$_2$CH$_2$— or —CH$_2$O—; and a wavy line (⁓) indicates that these bonds can be in the α- or β-positions possess thrombocyte inhibition properties.

14 Claims, No Drawings

1,4-OXATHIANES

SUMMARY OF THE INVENTION

It is an object of the present invention to provide new compounds which, in particular, can advantageously be used for the production of pharmaceuticals.

Upon further study of the specification and appended claims, further objects and advantages of this invention will become apparent to those skilled in the art.

These objects of this invention have been attained in a composition aspect, by providing 1,4-oxathianes of the formula I

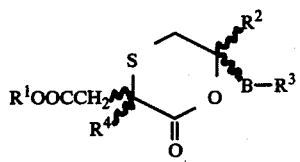

and the physiologically-acceptable salts thereof wherein $R^1$ is H or alkyl with 1–4 C-atoms; $R^2$ is H or alkyl with 1–4 C-atoms; $R^3$ is H, alkyl with 1–8 C-atoms, phenyl or phenyl substituted by F, Cl, Br, OH, $OCH_3$, $CF_3$ or $NO_2$; $R^4$ is H or $CH_3$; B is a single bond, $-CH_2-$, $-CH_2CH_2-$ or $-CH_2O-$; and a wavy line (⁓) indicates that these bonds can be in the α- or β-positions.

In another composition aspect, this invention relates to a pharmaceutical composition for treatment of thrombosis which comprises an amount of a compound of Formula I effective to inhibit thrombocyte aggregation and/or adhesion and a pharmaceutically acceptable adjuvant.

In a method-of-use aspect, this invention relates to a method for inhibiting thrombocyte aggregation and/or adhesion in mammals, including humans, which comprises administering an amount of a compound of formula I effective for this inhibition.

In a process aspect, this invention relates to processes for preparing the compounds of formula I.

In one method, a compound of formula II

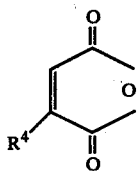

wherein $R^4$ is as defined above, is reacted with a compound of Formula III

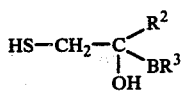

wherein $R^2$, $R^3$ and B are as defined above.

In a second method a compound of the formula IV

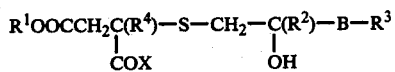

wherein X is OH, Cl, Br or I and $R^1$–$R^4$ and B are as defined above is reacted with an agent for splitting off HX.

DETAILED DISCUSSION

This invention relates to the compounds of formula I and their pharmacologically-acceptable salts, in which $R^1$–$R^4$ and B are as defined above.

In formula I and in the other formulae herein, a bond in the α-position is indicated by a dotted line and a bond in the β-position by an unbroken line. Bonds which are in the α- or β-positions are characterised by a wavy line.

The compounds of formula I contain at least one asymmetrical C-atom in the six membered ring; and when $R^2$ is not the same as $-B-R^3$, they contain two asymmetrical C-atoms in the six-membered ring. However, additional centers of asymmetry can also be present, for example, when $R^3$ is a branched alkyl radical with 3–8 C-atoms. Therefore, the compounds of formula I can occur in a plurality of stereoisomeric forms, and as a rule, they are present as racemic mixtures.

Apart from the individual racemates and racemic mixtures, this invention also includes the optically-active isomers of formula I and the physiologically-acceptable salts of these compounds.

In addition to hydrogen, $R^1$ can be an alkyl radical having 1–4 C-atoms, preferably unbranched, such as methyl, propyl, butyl or, especially, ethyl. Also included are branched alkyl radicals, such as isopropyl, isobutyl, sec-butyl or tert-butyl.

In addition to hydrogen, $R^2$ also can be an alkyl radical having 1–4 C-atoms, preferably unbranched, such as ethyl, propyl, butyl or, especially, methyl; it also includes branched alkyl radicals, such as isopropyl, isobutyl, sec-butyl or tert-butyl.

In addition to hydrogen, $R^3$ can also be an alkyl radical with 1–8 C-atoms, preferably an unbranched alkyl radical with 1–8 C-atoms and especially 3–5 C-atoms, such as methyl, ethyl, hexyl, heptyl, octyl, but especially propyl, butyl or pentyl. Furthermore, $R^3$ can also be a branched alkyl radical with 3–8 C-atoms which, in the main chain, preferably contains 3–5 C-atoms. For example, suitable $R^3$ groups include: isopropyl, 3-methylbutyl, 2-methylbutyl, 1-methylbutyl, 3,3-dimethylbutyl, 4-methylpentyl, 3-methylpentyl, 2-methylpentyl, 1-methylpentyl, 4,4-dimethylpentyl, 1,1-dimethylpentyl, 1-ethylpentyl, 5-methylhexyl, 5,5-dimethylhexyl.

In addition, $R^3$ can be phenyl or a phenyl radical substituted by F, Cl, Br, OH, $OCH_3$, $CF_3$ or $NO_2$. Singly substituted phenyl radicals are preferred, in particular, when they are substituted in the m- or p-position. Especially preferred substituted phenyl radicals $R^3$ are, p-fluorophenyl, p-chlorophenyl, m-chlorophenyl, m-bromophenyl, p-hydroxyphenyl, m-hydroxyphenyl, p-methoxyphenyl, m-methoxyphenyl, m-trifluoromethylphenyl, p-nitrophenyl, or m-nitrophenyl. Other monosubstituted phenyl radicals $R^3$ include, for example, o-fluorophenyl, m-fluorophenyl, o-chlorophenyl, p-bromophenyl, p-trifluoromethylphenyl and o-nitrophenyl. When $R^3$ is a multiply substituted phenyl radical, doubly substituted phenyl radicals and the 3,4,5-trimethoxyphenyl group are especially preferred. The doubly substituted phenyl radicals preferably contain two identical substituents. Suitable $R^3$ groups include 2,4-dichlorophenyl, 2,4-dibromophenyl, 2,4-dihydroxyphenyl, 3,4-dihydroxyphenyl and 2,4-dimethoxyphenyl. However, the $R^3$ phenyl radical can also be unequally substituted, including, for example, 2-chloro-4-nitrophenyl or 3-chloro-4-methoxyphenyl radicals.

When $R^3$ is H, B is preferably a C—H single bond, but can also be —$CH_2$—, —$CH_2CH_2$— or —$CH_2$—O—.

B is preferably a C—C single bond when $R^3$ is an alkyl radical with 1-8 C-atoms, but in this case, B can also be a —$CH_2$—, —$CH_2CH_2$— or —$CH_2O$— group. For the latter three embodiments, the B-$R^3$ grouping is an alkyl group which contains one or two C-atoms more than the $R^3$ group, thus preferably an unbranched alkyl group with 2-9 or 3-10 C-atoms, especially with 4-6 or 5-7 C-atoms, such as butyl, pentyl, hexyl or heptyl; a branched alkyl group with 4-9 or 5-10 C-atoms; or a preferably unbranched 2-oxaalkyl group with 2-9 C-atoms, especially with 4-6 C-atoms, such as 2-oxapentyl, 2-oxahexyl or 2-oxaheptyl.

When $R^3$ is phenyl or phenyl substituted by F, Cl, Br, OH, $OCH_3$, $CF_3$ or $NO_2$, B is preferably —$CH_2CH_2$— and especially —$CH_2O$— but can also be —$CH_2$— or a C—C single bond. In this case, the grouping —B—$R^3$ therefore preferably is phenoxymethyl, p-fluorophenoxymethyl, p-chlorophenoxymethyl, m-chlorophenoxymethyl, m-bromophenoxymethyl, p-hydroxyphenoxymethyl, m-hydroxyphenoxymethyl, p-methoxyphenoxymethyl, m-methoxyphenoxymethyl, m-trifluoromethylphenoxymethyl, p-nitrophenoxymethyl and m-nitrophenoxymethyl; however, also included are, for example m-fluorophenoxymethyl, o-chlorophenoxymethyl, o-nitrophenoxymethyl, 3,4,5-trimethoxyphenoxymethyl, 2,4-dichlorophenoxymethyl, 3,4-dihydroxyphenoxymethyl and 3-chloro-4-methoxyphenoxymethyl or the correspondingly substituted ethyl radicals, such as 2-phenylethyl-,2-p-fluorophenylethyl, 2-m-chlorophenylethyl, 2-m-bromophenylethyl,2-p-hydroxyphenylethyl, 2-m-methoxyphenylethyl or 2-m-nitrophenylethyl. Of course, the grouping —B—$R^3$ can also be a benzyl or phenyl group optionally substituted by F, Cl, Br, OH, $OCH_3$, $CF_3$ or $NO_2$.

$R^4$ is preferably hydrogen but can also be a methyl group.

Contemplated claimed compounds of formula I include those in which:

(a) $R^3$ is H or alkyl;
(b) $R^3$ is phenyl;
(c) $R^3$ is phenyl substituted by F, Cl, Br or $CF_3$;
(d) $R^3$ is phenyl substituted by OH, $OCH_3$ or $NO_2$;
(e) B is a single bond, —$CH_2$— or —$CH_2CH_2$—, including each of (a)-(d); and
(f) B is —$CH_2O$—, including each of (a)-(d).

Especially preferred are those compounds of the formula I in which at least one of $R^1$-$R^4$ and B is one of the foregoing preferred groups. Some of these preferred groups of compounds can be characterised by the following partial formulae I$a$ to I$f$ which otherwise correspond to formula I and in which the symbols not more closely defined have the meanings given in the formula I but in which in I$a$ $R^1$ = H,
in I$b$ $R^1$ = H and $R^4$ = H,
in I$c$ $R^1$ = H, $R^2$ = $CH_3$ and $R^4$ = H,
in I$d$ $R^1$ = H, $R^2$ = $CH_3$, $R^3$ = phenyl, m-chlorophenyl or m-trifluoromethylphenyl and $R^4$ = H, in I$e$ $R^1$ = H, $R^2$ = $CH_3$, $R^3$ = phenyl, m-chlorophenyl or m-trifluoromethylphenyl, $R^4$ = H and B = —$CH_2$—, —$CH_2CH_2$— or —$CH_2O$—, and
in I$f$ $R^1$ = H, $R^2$ = $CH_3$, $R^3$ = pentyl or 4-methylpentyl, $R^4$ = H and B = a C—C single bond.

In addition to the above-mentioned methods of preparing the compounds of formula I, several other preparative processes exist.

In one method, a compound of the formula I with $R^1$ = H, is reacted with an esterifying agent to convert it into another compound of the formula I with $R^1$ = alkyl having 1-4 C-atoms. Of course, the compounds of formula I can also be prepared by resolving a mixture of optical isomers into its racemates and/or enantiomers; by converting a compound of the formula I with $R^1$ = H, by reaction with a base, into one of its physiologically-acceptable salts; and/or by liberating the compound from such a salt by reaction with an acid.

For all of the following methods of preparing the various starting compounds, for use in each of the foregoing preparative methods, entirely conventional processes are involved. Appropriate reaction conditions can be found in standard works on preparative organic chemistry, e.g., HOUBEN-WEYL, *Methoden der organischen Chemie,* Georg-Thieme-Verlag, Stuttgart; or *ORGANIC SYNTHESES,* J. Wiley, New York - London - Sydney.

The compounds of formula II are known. They are simply maleic acid anhydride or citraconic acid anhydride (methylmaleic acid anhydride). The hydroxymercaptans of formula III and general processes for their preparation are known, for example from published German patent application No. 22,56,537, as well as from published German patent application Nos. 24,22,924 and 25,13,371.

The reaction of a compound of formula II with a compound of formula III preferably takes place in an inert organic solvent, for example, a hydrocarbon, such as petroleum ether or benzene; a chlorinated hydrocarbon, such as methylene chloride, 1,2-dichloroethane, perchlorobutadiene or chlorobenzene; or an ether, such as diethyl ether, diisopropyl ether, tetrahydrofuran or dioxane. The reaction is preferably conducted in the presence of a base, especially of an organic amine, such as diethylamine, triethylamine, diisopropylamine, dibutylamine, pyrrolidine, piperidine, dimethylaniline, pyridine, quinoline, etc. It can also be conducted in the presence of an inorganic base, for example of an alkali metal or alkaline earth metal hydroxide or of a basic salt, for example of an alkali metal carbonate, such as potassium carbonate or sodium carbonate. As a rule, suitable reaction temperature lies between about $-5°$ C. and about $+40°$ C., preferably room temperature. Suitable reaction times lie between about 15 minutes and about 3 hours.

The reaction is preferably carried out using stoichiometric amounts of II and III; an excess of one of these starting materials is not harmful, however. Thus, it can be advantageous to use an excess of the cheaper one of these reagents.

The manner of addition of the reagents is not critical.

The compounds of the formula IV are in part known and in part new. The new compounds of the formula IV can be prepared according to standard methods known from the literature from known preproducts. Is is, for example, possible to react maleic acid or citraconic acid monoalkyl esters with a thiol of the formula III and to convert the so obtained compound of the formula IV with X = OH, using fully conventional procedures, by treatment, for example, with phosphorus tribromide or thionyl chloride, into another compound of the formula IV with X = Br or Cl.

For the reaction of the compounds of formula IV, suitable agents for splitting off HX include bases, for example organic amines, especially the amines mentioned above as basic catalysts for the reaction of a compound of the formula II with a compound of the formula III. However, inorganic bases are also employable, preferably alkali metal or alkaline earth metal hydroxides, such as NaOH, KOH or Ca(OH)$_2$. It is also possible to use basic salts, especially alkali metal carbonates, such as sodium carbonate or potassium carbonate as the agent for splitting off HX. As a rule, the reaction is conducted using an inert organic solvent, preferably the solvents mentioned above for the reaction of a compound of formula II with a compound of formula III. Suitable reaction temperatures lie between 5° C. and about 60° C., preferably room temperature. Suitable reaction times lie at about 30 minutes to about 4 hours.

Compounds of formula I with $R^1$ = H can be esterified according to per se well known methods with an esterifying agent. Suitable esterifying agents include alcohols with up to 4 C-atoms, preferably in the presence of an inorganic or organic acid, such as HCl, HBr, HI, H$_2$SO$_4$, H$_3$PO$_4$, trifluoroacetic acid, or a sulphonic acid, such as benzene-sulphonic acid or p-toluenesulphonic acid, or in the presence of an acidic ion exchanger. Other suitable esterifying agents include diazoalkanes with up to 4 C-atoms, preferably diazomethane, alkyl halides with up to 4 C-atoms, preferably bromides, such as ethyl, propyl, isopropyl or butyl bromide, carboxylic acid or sulphonic acid alkyl esters, whereby the acid residue can be as desired and the alkyl radical contains up to 4 C-atoms.

The conventional esterifications occur for example in an inert, preferably water-free solvent, for example, an ether, such as diethyl ether, an alcohol, such as methanol or ethanol, or also in a hydrocarbon, such as petroleum ether, hexane, benzene or toluene, or in mixtures of these solvents. Suitable reaction times lie, as a rule, between 30 minutes and 24 hours. It is especially advantageous to carry out the esterifications using diazoalkanes, especially with diazomethane or diazoethane.

As discussed above, the compounds of formula I in general possess several centers of asymmetry but always at least one. Therefore, they are mostly obtained as mixtures of various stereoisomeric forms, i.e., as racemates or, as a rule, as mixtures of racemates. Since various racemates are diastereoisomeric to one another, they can, on the basis of their differing physical properties, be isolated from their mixtures and obtained in pure form. Suitable separation methods are conventional and include recrystallisation from suitable solvents (whereby, instead of the compounds themselves, there can also be used well crystallising derivatives), distillative separation, and especially chromatographic separation, including adsorption chromatographic and partition chromatographic methods.

The racemates can be separated into their optical antipodes using any of a plurality of conventional methods, as described in the literature. The method of chemical separation is preferred. According to this technique, diastereomers are formed from the racemic mixture by reaction with an optically-active adjuvant.

Thus, an optically-active base can be reacted with the carboxyl group of a compound of formula I. For example, diastereomeric salts of the compounds of formula I with $R^1$ = H can be formed with optically-active amines, such as quinine, brucine, 1-phenylethylamine, 1-($\alpha$-naphthyl)-ethylamine or basic amino acids, such as lysine, arginine, etc. The difference in the solubility of the diastereomeric salts obtained permits the selective crystallisation of one form and the regeneration of the particular optically-active compounds from the mixture.

The free carboxylic acids of formula I with $R^1$ = H can be converted by reaction with a base, into one of their physiologically acceptable metal or ammonium salts. Suitable such salts especially include sodium, potassium, magnesium, calcium and ammonium salts, substituted ammonium salts, such as dimethyl and diethyl ammonium, monoethanol, diethanol and triethanol ammonium, cyclohexyl ammonium, dicyclohexyl ammonium and dibenzyl ethylene diammonium salts. On the other hand, acids of formula I can be liberated from their metal and ammonium salts by treatment with acids, especially mineral acids, such as hydrochloric or sulphuric acid.

It has been found that the compounds of formula I possess valuable pharmacological properties. In particular, they exhibit thrombocyte aggregation-inhibiting and thrombocyte adhesion-inhibiting properties which can be demonstrated, for example, analogously to the method of Born, Nature (London), 194 (1962). Thus, the compounds of formula I can be used as pharmaceuticals. In addition they can also be used as intermediates for the preparation of other pharmaceuticals.

Also the subject of the invention are medicinal agents which contain carrier and adjuvant materials conventional in pharmacy, and comprising at least one compound of formula I. Such medicinal agents are conventionally prepared by formulating into suitable dosage form at least one compound of formula I, together with at least one carrier or adjuvant material conventional in pharmacy and optionally together with an additional active material.

To prepare such agents, the new compounds of formula I can be mixed with at least one solid, liquid and/or semi-liquid carrier or adjuvant material conventional in pharmacy. The mixtures or the compounds of formula I with the carrier or adjuvant materials customary in pharmacy can be used in human or veterinary medicine. Suitable carrier materials include the organic and inorganic materials which are suitable for parenteral, enteral (e.g., oral) or topical administration and which do not react with the new compounds of formula I, for example, water, vegetable oils, benzyl alcohols, polyethylene glycols, glycerol triacetate, gelatine, lactose, starch, magnesium stearate, talc, vaseline, cholesterol, etc. For oral administration, tablets, dragees, capsules, syrups, juices or drops are suitable, for rectal administration suppositories are suitable; for parenteral administration solutions, preferably oily or aqueous solutions, or suspensions, emulsions or implants are suitable; and for topical administration salves, creams or powders are suitable.

The new compounds can also by lyophilised and the lyophilisates obtained can be employed, e.g., for the preparation of injection preparations. The compositions of this invention can be sterilized or mixed with adjuvant materials, such as lubricant, preserving, stabilising or wetting agents, emulsifiers, salts which influence the osmotic pressure, buffer substances, coloring, flavoring and/or aroma generating materials. If desired, one or more additional active materials, e.g., one or more vitamins can be included.

The substances according to the invention are, as a rule, administered in fully analogous manner to known thrombosis prophylactics which are commercially available, for example in dosages between about 1 and 500 mg, especially between 5 and 50 mg per dosage unit. The daily dosage preferably lies between about 0.02 and 10 mg/kg of body weight. The specific dose for a particular patient depends, however, upon the usual diversity of factors, for example, upon the effectiveness of the specific compound used, upon the age, body weight, general state of health, sex and diet of the patient, upon the time and route of administration, upon the speed of excretion, upon the combination of medicaments and upon the severity of the particular disease for which the therapy is being used, inter alia. Oral administration is preferred.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever. In the following examples, all temperatures are set forth uncorrected in degrees Celsius; unless otherwise indicated, all parts and percentages are by weight.

Each of the compounds of formula I mentioned in the following Examples is especially suitable for the preparation of pharmaceutical compositions.

The NMR spectra (NMR) were measured in $CDCl_3$ against tetramethylsilane and are characterised by specification of the signals in ppm; wherein $m$ = multiplet, $q$ = quartet, $t$ = triplet, $d$ = doublet and $s$ = singlet.

EXAMPLE 1

Into a mixture consisting of 10 g of maleic acid anhydride, 8.5 g of 2-hydroxy-2-methylheptane-1-thiol and 105 ml of methylene chloride, 1 ml of diisopropylamine, dissolved in 5 ml of methylene chloride is dropped. During this step the temperature is maintained at equal to or less than 30°. An additional 8.5 g of 2-hydroxy-2-methylheptane-1-thiol, dissolved in 5 ml of methylene chloride is added. After 15 minutes the usual work-up is performed. (Usual working up refers to the following procedure throughout the examples: washing of the organic phase with 1% aqueous sulphuric acid and with water; drying of the organic phase over $MgSO_4$; distilling off the solvent; and chromatographic purification of the residue on silica gel with chloroform or ether:petroleum ether = 2:8 as elution agent.) 6-pentyl-6-methyl-2-oxo-1,4-oxathiane-3-acetic acid is obtained: NMR: 3.88 (q), 1.54 (s), 0.9 (t).

EXAMPLES 2–34

Analogously to Example 1, by reaction of maleic acid anhydride with the corresponding 2-hydroxy-2-methylthiol of formula III ($R^2$ = methyl) in the presence of diisopropylamine, there are obtained the compounds of formula I of the following Examples 2 to 34:

| Example | —B—$R^3$ in the compounds of formula III | compound of formula I |
| --- | --- | --- |
| 2 | H | 6-methyl-2-oxo-1,4-oxathiane-3-acetic acid |
| 3 | methyl | 6,6-dimethyl-2-oxo-1,4-oxathiane-3-acetic acid |
| 4 | ethyl | 6-ethyl-6-methyl-2-oxo-1,4-oxathiane-3-acetic acid |
| 5 | propyl | 6-propyl-6-methyl-2-oxo-1,4-oxathiane-3-acetic acid |
| 6 | butyl | 6-butyl-6-methyl-2-oxo-1,4-oxathiane-3-acetic acid |
| 7 | hexyl | 6-hexyl-6-methyl-2-oxo-1,4-oxathiane-3-acetic acid |
| 8 | heptyl | 6-heptyl-6-methyl-2-oxo-1,4-oxathiane-3-acetic acid |
| 9 | octyl | 6-octyl-6-methyl-2-oxo-1,4-oxathiane-3-acetic acid |
| 10 | 4-methylpentyl | 6-(4-methylpentyl)-6-methyl-2-oxo-1,4-oxathiane-3-acetic acid NMR: 4.0 (m), 1.63 (s), 1.0 (s), 0.92 (s), |
| 11 | 4,4-dimethylpentyl | 6-(4,4-dimethylpentyl)-6-methyl-2-oxo-1,4-oxathiane-3-acetic acid |
| 12 | m-chlorobenzyl | 6-m-chlorobenzyl-6-methyl-2-oxo-1,4-oxathiane-3-acetic acid |
| 13 | p-fluorobenzyl | 6-p-fluorobenzyl-6-methyl-2-oxo-1,4-oxathiane-3-acetic acid |
| 14 | m-trifluoromethylbenzyl | 6-m-trifluoromethylbenzyl-6-methyl-2-oxo-1,4-oxathiane-3-acetic acid |
| 15 | benzyl | 6-benzyl-6-methyl-2-oxo-1,4-oxathiane-3-acetic acid, NMR: 7.22 (m), 3.8 (m), 1.55 (s) |
| 16 | 2-phenylethyl | 6-(2-phenylethyl)-6-methyl-2-oxo-1,4-oxathiane-3-acetic acid, NMR: 7.2 (m), 3.92 (s), 1.63 (s) |
| 17 | 2-m-chlorophenylethyl | 6-(2-m-chlorophenylethyl)-6-methyl-2-oxo-1,4-oxathiane-3-acetic acid, NMR: 3.91 (m), 1.61 (s) |
| 18 | 2-p-fluorophenylethyl | 6-(2-p-fluorophenylethyl)-6-methyl-2-oxo-1,4-oxathiane-3-acetic acid, |
| 19 | 2-m-methoxyphenylethyl | 6-(2-m-methoxyphenylethyl)-6-methyl-2-oxo-1,4-oxathiane-3-acetic acid |
| 20 | 2-p-nitrophenylethyl | 6-(2-p-nitrophenylethyl)-6-methyl-2-oxo-1,4-oxathiane-3-acetic acid |

-continued

| Example | —B—R³ in the compounds of formula III | compound of formula I |
|---|---|---|
| 21 | 2-m-trifluoro-methylphenylethyl | 6-(2-m-trifluoromethylphenylethyl)-6-methyl-2-oxo-1,4-oxathiane-3-acetic acid, NMR: 3.88 (m), 1.61 (s) |
| 22 | 2-m-bromophenyl-ethyl | 6-(2-m-bromophenylethyl)-6-methyl-2-oxo-1,4-oxathiane-3-acetic acid |
| 23 | 2-p-hydroxyphenyl-ethyl | 6-(2-p-hydroxyphenylethyl)-6-methyl-2-oxo-1,4-oxathiane-3-acetic acid |
| 24 | phenoxymethyl | 6-phenoxymethyl-6-methyl-2-oxo-1,4-oxathiane-3-acetic acid |
| 25 | m-fluorophenoxy-methyl | 6-m-fluorophenoxymethyl-6-methyl-2-oxo-1,4-oxathiane-3-acetic acid |
| 26 | o-chlorophenoxy-methyl | 6-o-chlorophenoxymethyl-6-methyl-2-oxo-1,4-oxathiane-3-acetic acid |
| 27 | m-chlorophenoxy-methyl | 6-m-chlorophenoxymethyl-6-methyl-2-oxo-1,4-oxathiane-3-acetic acid |
| 28 | p-chlorophenoxy-methyl | 6-p-chlorophenoxymethyl-6-methyl-2-oxo-1,4-oxathiane-3-acetic acid |
| 29 | 3,4,5-trimethoxy-phenoxymethyl | 6-(3,4,5-trimethoxyphenoxymethyl)-6-methyl-2-oxo-1,4-oxathiane-3-acetic acid |
| 30 | m-hydroxyphenoxy-methyl | 6-m-hydroxyphenoxymethyl-6-methyl-2-oxo-1,4-oxathiane-3-acetic acid |
| 31 | o-nitrophenoxy-methyl | 6-o-nitrophenoxymethyl-6-methyl-2-oxo-1,4-oxathiane-3-acetic acid |
| 32 | m-nitrophenoxy-methyl | 6-m-nitrophenoxymethyl-6-methyl-2-oxo-1,4-oxathiane-3-acetic acid |
| 33 | p-trifluoromethyl-phenoxymethyl | 6-p-trifluoromethylphenoxymethyl-6-methyl-2-oxo-1,4-oxathiane-3-acetic acid |
| 34 | m-trifluoromethyl-phenoxymethyl | 6-m-trifluoromethylphenoxymethyl-6-methyl-2-oxo-1,4-oxathiane-3-acetic acid, NMR: 3.95 (m), 1.66 (s). |

EXAMPLE 35

Analogously to Example 1, by reaction of maleic acid anhydride with 2-hydroxyethanethiol in the presence of piperidine (instead of diisopropylamine) and the usual working up, 2-oxo-1,4-oxathiane-3-acetic acid, m.p. = 96°–98° is obtained.

EXAMPLES 36–64

Analogously to Example 35, there are obtainable, by reaction of maleic acid anhydride with the corresponding 2-hydroxythiol of formula III ($R^2$ = H) in the presence of piperidine, the compounds of formula I of Examples 36 to 64:

| Example | —B—R³ in the compounds of formula III | compound of formula I |
|---|---|---|
| 36 | ethyl | 6-ethyl-2-oxo-1,4-oxathiane-3-acetic acid |
| 37 | butyl | 6-butyl-2-oxo-1,4-oxathiane-3-acetic acid |
| 38 | pentyl | 6-pentyl-2-oxo-1,4-oxathiane-3-acetic acid |
| 39 | 1-methylpentyl | 6-(1-methylpentyl)-2-oxo-1,4-oxathiane-3-acetic acid |
| 40 | 4-methylpentyl | 6-(4-methylpentyl)-2-oxo-1,4-oxathiane-3-acetic acid |
| 41 | 4,4-dimethylpentyl | 6-(4,4-dimethylpentyl)-2-oxo-1,4-oxathiane-3-acetic acid |
| 42 | hexyl | 6-hexyl-2-oxo-1,4-oxathiane-3-acetic acid |
| 43 | octyl | 6-octyl-2-oxo-1,4-oxathiane-3-acetic acid |
| 44 | benzyl | 6-benzyl-2-oxo-1,4-oxathiane-3-acetic acid |
| 45 | p-chlorobenzyl | 6-p-chlorobenzyl-2-oxo-1,4-oxathiane-3-acetic acid |
| 46 | m-chlorobenzyl | 6-m-chlorobenzyl-2-oxo-1,4-oxathiane-3-acetic acid |
| 47 | p-fluorobenzyl | 6-p-fluorobenzyl-2-oxo-1,4-oxathiane-3-acetic acid |
| 48 | m-bromobenzyl | 6-m-bromobenzyl-2-oxo-1,4-oxathiane-3-acetic acid |
| 49 | m-hydroxybenzyl | 6-m-hydroxybenzyl-2-oxo-1,4-oxathiane-3-acetic acid |
| 50 | m-methoxybenzyl | 6-m-methoxybenzyl-2-oxo-1,4-oxathiane-3-acetic acid |
| 51 | p-trifluoromethylbenzyl | 6-p-trifluoromethylbenzyl-2-oxo-1,4-oxathiane-3-acetic acid |
| 52 | 2-phenylethyl | 6-(2-phenylethyl)-2-oxo-1,4-oxathiane-3-acetic acid |
| 53 | 2-m-chlorophenyl-ethyl | 6-(2-m-chlorophenylethyl)-2-oxo-1,4-oxathiane-3-acetic acid |
| 54 | 2-p-fluorophenyl- | 6-(2-p-fluorophenylethyl)-2-oxo-1,4- |

-continued

| Example | —B—R³ in the compounds of formula III | compound of formula I |
|---|---|---|
| | ethyl | oxathiane-3-acetic acid |
| 55 | 2-m-trifluoro-methylphenylethyl | 6-(2-m-trifluoromethylphenylethyl)-2-oxo-1,4-oxathiane-3-acetic acid |
| 56 | 2-m,p-dimethoxy-phenylethyl | 6-(2-m,p-dimethoxyphenylethyl)-2-oxo-1,4-oxathiane-3-acetic acid |
| 57 | phenoxymethyl | 6-phenoxymethyl-2-oxo-1,4-oxathiane-3-acetic acid |
| 58 | o-chlorophenoxy-methyl | 6-o-chlorophenoxymethyl-2-oxo-1,4-oxathiane-3-acetic acid |
| 59 | p-chlorophenoxy-methyl | 6-p-chlorophenoxymethyl-2-oxo-1,4-oxathiane-3-acetic acid |
| 60 | m-methoxyphenoxy-methyl | 6-m-methoxyphenoxymethyl-2-oxo-1,4-oxathiane-3-acetic acid |
| 61 | m-nitrophenoxy-methyl | 6-m-nitrophenoxymethyl-2-oxo-1,4-oxathiane-3-acetic acid |
| 62 | m-hydroxyphenoxy-methyl | 6-m-hydroxyphenoxymethyl-2-oxo-1,4-oxathiane-3-acetic acid |
| 63 | m-trifluoromethyl-phenoxymethyl | 6-m-trifluoromethylphenoxymethyl-2-oxo-1,4-oxathiane-3-acetic acid |
| 64 | p-bromophenoxy-methyl | 6-p-bromophenoxymethyl-2-oxo-1,4-oxathiane-3-acetic acid |

EXAMPLE 65

Analogously to Example 1, from maleic acid anhydride and 2-hydroxy-3-m-chlorophenoxypropane-1-thiol in the presence of diisopropylamine and the usual working up of the reaction mixture, 6-m-chlorophenoxymethyl-2-oxo-1,4-oxathiane-3-acetic acid is obtained. It is separated into two isomers using chromatographic purification:

isomer A: m.p. = 153°–154° isomer B: oil, IR: 1720, 1595, 1480, 1280, 1230, 1170 cm$^{-1}$.

EXAMPLE 66

Analogously to Example 1, from citraconic acid anhydride and 2-hydroxy-2-methylheptane-1-thiol in the presence of diisopropylamine and the usual working up of the reaction mixture, 3,6-dimethyl-2-oxo-6-pentyl-1,4-oxathiane-3-acetic acid is obtained. Using chromatographic purification it can be separated into two isomers:

isomer A (polar): 1.64 (s), 1.54 (s), 0.9 (t),
isomer B (non-polar): 1.68 (s), 1.50 (s), 0.9 (t).

EXAMPLE 67

To 4.7 g of 6-pentyl-6-methyl-2-oxo-1,4-oxathiane-3-acetic acid, dissolved in 50 ml of diethyl ether, there is added dropwise, with stirring and ice cooling, ethereal diazomethane solution, until a pale yellow color just remained. After the usual working up, 6-pentyl-6-methyl-2-oxo-1,4-oxathiane-3-acetic acid methyl ester is obtained:

NMR: 4.9 (m), 3.76 (s), 1.54 (s), 0.9 (t).

EXAMPLES 68–83

From the compounds of the formula I (R¹ = H) mentioned in Examples 2–66, there are obtained analogously by reaction with diazomethane, the corresponding methyl esters, especially the methyl esters of formula I mentioned in the following Examples 68 to 83:

| Ex. | methyl ester of formula I |
|---|---|
| 68 | 2-oxo-1,4-oxathiane-3-acetic acid methyl ester |
| 69 | 6-pentyl-2-oxo-1,4-oxathiane-3-acetic acid methyl ester |
| 70 | 6-benzyl-2-oxo-1,4-oxathiane-3-acetic acid methyl ester |
| 71 | 6-m-chlorobenzyl-2-oxo-1,4-oxathiane-3-acetic acid methyl ester |
| 72 | 6-(2-phenylethyl)-2-oxo-1,4-oxathiane-3-acetic acid methyl ester |

-continued

| Ex. | methyl ester of formula I |
|---|---|
| 73 | 6-(2-m-chlorophenylethyl)-2-oxo-1,4-oxathiane-3-acetic acid methyl ester |
| 74 | 6-phenoxymethyl-2-oxo-1,4-oxathiane-3-acetic acid methyl ester |
| 75 | 6-m-chlorophenoxymethyl-2-oxo-1,4-oxathiane-3-acetic acid methyl ester |
| 76 | 6-methyl-2-oxo-1,4-oxathiane-3-acetic acid methyl ester |
| 77 | 6-heptyl-6-methyl-2-oxo-1,4-oxathiane-3-acetic acid methyl ester |
| 78 | 6-benzyl-6-methyl-2-oxo-1,4-oxathiane-3-acetic acid methyl ester |
| 79 | 6-m-chlorobenzyl-6-methyl-2-oxo-1,4-oxathiane-3-acetic acid methyl ester |
| 80 | 6-(2-phenylethyl)-6-methyl-2-oxo-1,4-oxathiane-3-acetic acid methyl ester |
| 81 | 6-(2-m-chlorophenylethyl)-6-methyl-2-oxo-1,4-oxathiane-3-acetic acid methyl ester |
| 82 | 6-phenoxymethyl-6-methyl-2-oxo-1,4-oxathiane-3-acetic acid methyl ester |
| 83 | 6-m-chlorophenoxymethyl-6-methyl-2-oxo-1,4-oxathiane-3-acetic acid methyl ester |

EXAMPLE 84

Analogously to Example 67, by the reaction of 6-pentyl-6-methyl-2-oxo-1,4-oxathiane-3-acetic acid with diazoethane and the usual working up, there is obtainable 6-pentyl-6-methyl-2-oxo-1,4-oxathiane-3-acetic acid ethyl ether.

EXAMPLE 85

To 2.60 g of 6-pentyl-6-methyl-2-oxo-1,4-oxathiane-3-acetic acid, dissolved in 16 ml of dry ethanol, there is added dropwise a solution of sodiumm ethylate, prepared from 0.23 g of sodium and 8 ml of dry ethanol. The solvent is distilled off and the sodium salt of 6-pentyl-6-methyl-2-oxo-1,4-oxathiane-3-acetic acid is obtained as the residue.

EXAMPLE 86

1.41 g of the sodium salt of 6-pentyl-6-methyl-2-oxo-1,4-oxathiane-3-acetic acid and 0.63 g of 1-bromopropane are boiled for 1 hour in a mixture of 15 ml of dry ethanol and 5 ml of dry diethyl ether. The mixture is further stirred for 1 hour at room temperature. It is permitted to stand for about 12 hours at 0° and filtered. After distilling off the solvent, 6-pentyl-6-methyl-2-oxo-1,4-oxathiane-3-acetic acid n-propyl ester is obtained.

By reaction of 6-pentyl-6-methyl-2-oxo-1,4-oxathiane-3-acetic acid with 1-bromobutane, there is analogously obtained 6-pentyl-6-methyl-2-oxo-1,4-oxathiane-3-acetic acid n-butyl ester.

EXAMPLES 87–105

Analogously to Example 66, from citraconic acid anhydride and the corresponding 2-hydroxy-2-methylthiols of formuls III ($R^2$ = methyl), there are obtainable the compounds of formula I of the following Examples 87 to 105:

| Example | —B—$R^3$ in the compounds of formula III | compound of formula I |
|---|---|---|
| 87 | H | 3,6-dimethyl-2-oxo-1,4-oxathiane-3-acetic acid |
| 88 | methyl | 3,6,6-trimethyl-2-oxo-1,4-oxathiane-3-acetic acid |
| 89 | 4-methylpentyl | 6-(4-methyhlpentyl)-3,6-dimethyl-2-oxo-1,4-oxathiane-3-acetic acid |
| 90 | hexyl | 6-hexyl-3,6-dimethyl-2-oxo-1,4-oxathiane-3-acetic acid |
| 91 | heptyl | 6-heptyl-3,6-dimethyl-2-oxo-1,4-oxathiane-3-acetic acid |
| 92 | octyl | 6-octyl-3,6-dimethyl-2-oxo-1,4-oxathiane-3-acetic acid |
| 93 | benzyl | 6-benzyl-3,6-dimethyl-2-oxo-1,4-oxathiane-3-acetic acid |
| 94 | m-chlorobenzyl | 6-m-chlorobenzyl-3,6-dimethyl-2-oxo-1,4-oxathiane-3-acetic acid |
| 95 | m-trifluoromethyl-benzyl | 6-m-trifluoromethylbenzyl-3,6-dimethyl-2-oxo-1,4-oxathiane-3-acetic acid |
| 96 | p-fluorobenzyl | 6-p-fluorobenzyl-3,6-dimethyl-2-oxo-1,4-oxathiane-3-acetic acid |
| 97 | 2-phenylethyl | 6-(2-phenylethyl)-3,6-dimethyl-2-oxo-1,4-oxathiane-3-acetic acid |
| 98 | 2-m-chlorophenyl-ethyl | 6-(2-m-chlorophenylethyl)-3,6-dimethyl-2-oxo-1,4-oxathiane-3-acetic acid |
| 99 | 2-m-trifluoromethyl-phenylethyl | 6-(2-m-trifluoromethylphenylethyl)-3,6-dimethyl-2-oxo-1,4-oxathiane-3-acetic acid |
| 100 | 2-p-fluorophenyl-ethyl | 6-(2-p-fluorophenylethyl)-3,6-dimethyl-2-oxo-1,4-oxathiane-3-acetic acid |
| 101 | phenoxymethyl | 6-phenoxymethyl-3,6-dimethyl-2-oxo-1,4-oxathiane-3-acetic acid |
| 102 | m-chlorophenoxy-methyl | 6-m-chlorophenoxymethyl-3,6-dimethyl-2-oxo-1,4-oxathiane-3-acetic acid |
| 103 | m-trifluoromethyl-phenoxymethyl | 6-m-trifluoromethylphenoxymethyl-3,6-dimethyl-2-oxo-1,4-oxathiane-3-acetic acid |
| 104 | m-fluorophenoxy-methyl | 6-p-fluorophenoxymethyl-3,6-dimethyl-2-oxo-1,4-oxathiane-3-acetic acid |
| 105 | o-chlorophenoxy-methyl | 6-o-chlorophenoxymethyl-3,6-dimethyl-2-oxo-1,4-oxathiane-3-acetic acid |

EXAMPLES 106–119

Analogously to Example 66, from citraconic acid anhydride and the corresponding 2-hydroxythiols of formula III ($R^2$ = H), there are obtainable the compounds of formula I of the following Examples 106 to 119.

| Example | —B—$R^3$ in the compounds of formula III | compound of formula I |
|---|---|---|
| 106 | H | 3-methyl-2-oxo-1,4-oxathiane-3-acetic acid |
| 107 | butyl | 6-butyl-3-methyl-2-oxo-1,4-oxathiane-3-acetic acid |
| 108 | pentyl | 6-pentyl-3-methyl-2-oxo-1,4-oxathiane-3-acetic acid |
| 109 | 4-methylpentyl | 6-(4-methylpentyl)-3-methyl-2-oxo-1,4-oxathiane-3-acetic acid |
| 110 | octyl | 6-octyl-3-methyl-2-oxo-1,4-oxathiane-3-acetic acid |
| 111 | benzyl | 6-benzyl-3-methyl-2-oxo-1,4-oxathiane-3-acetic acid |
| 112 | m-chlorobenzyl | 6-m-chlorobenyl-3-methyl-2-oxo-1,4-oxathiane-3-acetic acid |
| 113 | m-trifluoromethyl-benzyl | 6-m-trifluoromethylbenzyl-3-methyl-2-oxo-1,4-oxathiane-3-acetic acid |
| 114 | 2-phenylethyl | 6-(2-phenylethyl)-3-methyl-2-oxo-1,4-oxathiane-3-acetic acid |
| 115 | 2-m-chlorophenyl-ethyl | 6-(2-m-chlorophenylethyl)-3-methyl-2-oxo-1,4-oxathiane-3-acetic acid |
| 116 | 2-m-trifluoromethyl-phenylethyl | 6-(2-m-trifluoromethylphenylethyl)-2-oxo-1,4-oxathiane-3-acetic acid |
| 117 | phenoxymethyl | 6-phenoxymethyl-3-methyl-2-oxo-1,4-oxathiane-3-acetic acid |
| 118 | m-chlorophenoxy-methyl | 6-m-chlorophenoxymethyl-3-methyl-2-oxo-1,4-oxathiane-3-acetic acid |
| 119 | m-trifluoromethyl-phenoxymethyl | 6-m-trifluoromethylphenoxymethyl-3-methyl-2-oxo-1,4-oxathiane-3-acetic acid |

EXAMPLE 120

(a) A mixture of 2.6 g of maleic acid monomethyl ester, 3.2 g of 2-hydroxy-2-methylheptane-1-thiol, 0.5 ml of pyridine and 120 ml of methylene chloride is stirred for 3 hours at 30°. After the usual working up, 6-hydroxy-3-hydroxycarbonyl-6-methyl-4-thiaundecanoic acid methyl ester is obtained.

(b) 2.7 g of 6-hydroxy-3-hydroxycarbonyl-6-methyl-4-thiaundecanoic acid methyl ester is boiled with 3.3 g of α,α-dipyridyl disulphide and 5.4 g of triphenyl phosphine for 5 hours in 105 ml of xylene. After the usual working up, 6-pentyl-6-methyl-2-oxo-1,4-oxathiane-3-acetic acid is obtained NMR: 3.88 (q), 1.54 (s), 0.9 (t).

(c) 2.7 g of 6-hydroxy-3-hydroxycarbonyl-6-methyl-4-thiaundecanoic acid methyl ester and 1.25 g of SOCl$_2$ are stirred for 2 hours in 40 ml of chloroform at room temperature. The mixture is boiled briefly. After cooling, 0.5 ml of piperidine, dissolved in 20 ml of chloroform is added thereto. The resultant mixture is further stirred for 1 hour at 30°. After the usual working up, 6-pentyl-6-methyl-2-oxo-1,4-oxathiane-3-acetic acid is obtained.

NMR: 3,88 (q), 1.54 (s), 0.9 (t).

The following Examples concern mixtures of compounds of formula I with carrier or adjuvant materials customary in pharmacy. The compositions can be used especially as pharmaceuticals:

EXAMPLE A: Tablets

A mixture, consisting of 30 g of the sodium salt of 6-pentyl-6-methyl-2-oxo-1,4-oxathiane-3-acetic acid, 50 g of lactose, 16 g of maize starch, 2 g of cellulose powder and 2 g of magnesium stearate, is conventionally pressed into tablets in such a manner that each tablet contains 10 mg of the active material.

EXAMPLE B: Dragees

Tablets are pressed analogously to Example A and subsequently conventionally coated with a coating consisting of sugar, maize starch, talc and tragacanth.

EXAMPLE C: Ampoules 10 g of 6-pentyl-6-methyl-2-oxo-1,4-oxathiane-3-acetic acid is dissolved in a mixture of 9.5 liters of doubly distilled water and 0.5 liter of ethylene glycol. The mixture is sterile filtered. Under sterile conditions, the resultant solution is filled in 13 ml amounts into ampoules which are subsequently heat sealed.

Tablets, dragees and ampoules containing one or more of the other active materials of formula I can be obtained analogously.

The preceding examples can be repeated with similar success by substituting the generically or specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. A 1,4-oxathiane of the formula

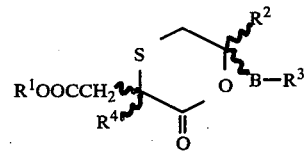

and its physiologically acceptable salts
wherein $R^1$ is H or alkyl having 1–4 C-atoms; $R^2$ is H or alkyl having 1–4 C-atoms; $R^3$ is H, alkyl having 1–8 C-atoms, phenyl or phenyl substituted by F, Cl, Br, OH, OCH$_3$, CF$_3$ or NO$_2$; $R^4$ is H or CH$_3$; B is a single bond, —CH$_2$—, —CH$_2$CH$_2$— or —CH$_2$O—; and a wavy line (∿) indicates a bond which can be in the α- or β-position.

2. The oxathianes of claim 1 wherein $R^1$ is H and $R^4$ is H.

3. The oxathianes of claim 1 wherein $R^2$ is CH$_3$.

4. The oxathianes of claim 2 wherein $R^2$ is CH$_3$.

5. The oxathianes of claim 1 wherein $R^3$ is phenyl, m-chlorophenyl or m-trifluoromethylphenyl and B is —CH$_2$—, —CH$_2$CH$_2$— or —CH$_2$O—.

6. The oxathianes of claim 1 wherein $R^3$ is pentyl or 4-methylpentyl, $R^4$ is H and B is a C—C single bond.

7. 6-Pentyl-6-methyl-2-oxo-1,4-oxathiane-3-acetic acid, a compound of claim 1.

8. 6-Pentyl-6-methyl-2-oxo-1,4-oxathiane-3-acetic acid methyl ester, a compound of claim 1.

9. 6-Benzyl-6-methyl-2-oxo-1,4-oxathiane-3-acetic acid, a compound of claim 1.

10. 6-(2-m-Chlorophenylethyl)-6-methyl-2-oxo-1,4-oxathiane-3-acetic acid, a compound of claim 1.

11. 6-m-Trifluoromethylphenoxymethyl-6-methyl-2-oxo-1,4-oxathiane-3-acetic acid, a compound of claim 1.

12. 6-Pentyl-3,6-dimethyl-2-oxo-1,4-oxathiane-3-acetic acid, a compound of claim 1.

13. A pharmaceutical composition which comprises an amount of an oxathiane of claim 1 effective to inhibit thrombocyte agglomeration and a pharmaceutically acceptable adjuvant.

14. A method of inhibiting thrombocyte agglomeration which comprises administering to a mammal an antithrombotically effective amount of an oxathiane of claim 1.

* * * * *